United States Patent
Herve et al.

(10) Patent No.: US 6,857,640 B2
(45) Date of Patent: Feb. 22, 2005

(54) DUAL-ENERGY RADIOGRAPHY PROCESS DIFFERENTIATING BONE TISSUES, LEAN TISSUES AND FATTY TISSUES

(75) Inventors: Lionel Herve, Grenoble (FR); Christine Robert-Coutant, St Martin d'uriage (FR); Jean-Marc Dinten, Lyons (FR)

(73) Assignee: Commissariat a l'Energie Atomique, Paris (FR)

( * ) Notice: Subject to any disclaimer, the term of this patent is extended or adjusted under 35 U.S.C. 154(b) by 100 days.

(21) Appl. No.: 10/314,210

(22) Filed: Dec. 9, 2002

(65) Prior Publication Data

US 2003/0133538 A1 Jul. 17, 2003

(30) Foreign Application Priority Data

Dec. 7, 2001 (FR) .......................................... 01 15849

(51) Int. Cl.$^7$ .............................................. G01N 23/06
(52) U.S. Cl. ................... 278/53; 378/54; 378/5
(58) Field of Search ............... 378/54, 53, 5, 378/37, 98.9

(56) References Cited

U.S. PATENT DOCUMENTS

| | | | | |
|---|---|---|---|---|
| 5,155,365 | A | * 10/1992 | Cann et al. | 250/363.02 |
| 5,465,284 | A | 11/1995 | Karellas | 378/62 |
| 5,917,877 | A | 6/1999 | Chiabrera et al. | 378/53 |
| 5,949,846 | A | * 9/1999 | Stein et al. | 378/54 |
| 6,052,433 | A | * 4/2000 | Chao | 378/98.9 |
| 6,173,034 | B1 | 1/2001 | Chao | 378/37 |
| 6,205,348 | B1 | 3/2001 | Giger et al. | 600/407 |
| 6,282,258 | B1 | 8/2001 | Stein et al. | 378/54 |
| 6,516,045 | B2 | * 2/2003 | Shepherd et al. | 378/53 |
| 2003/0026385 | A1 | * 2/2003 | Dinten et al. | 378/98.9 |

FOREIGN PATENT DOCUMENTS

WO    WO 00/21441    4/2000

OTHER PUBLICATIONS

Journal Phys. Med. Biol., vol. 39, "Theoretical and Experimental Limits of Triple Photon Energy Absorptiometry in the Measurement of Bone Mineral", *Kotzki et al.*, 1991, pp. 429–737.

Med. Phys., vol. 175 (5), "Effect of Nomineral Tissues on Measurement of Bone Mineral Content by Dual–Photon Absorptionmetry", *Sorenson et al.*, 1990, pp. 905–912.

Med. Biol., vol. 35 (7), "Dual–Photon Absorptiometry for Determination of Bone Mineral Content in the Calcaneus with Correction of Fat", *Jonson et al.*, 1990, pp. 961–969.

* cited by examiner

*Primary Examiner*—Craig E. Church
*Assistant Examiner*—Irakli Kiknadze
(74) *Attorney, Agent, or Firm*—Oblon, Spivak, McClelland, Maier & Neustadt, P.C.

(57) ABSTRACT

This radiography process utilizes dual-energy rays and comprises, in order to differentiate bone, lean and fatty tissues at the same time, an improvement consisting in assessing the total length penetrated by each ray while correcting the errors which may be produced by internal gas pockets. One proceeds as follows: selection of certain rays which have not penetrated bone tissues; calculation of the thicknesses of lean and fatty tissues penetrated by these rays according to the two attenuations, the sum of these two thicknesses being the length of attenuation; estimation of the length of attenuation elsewhere, in particular by means of interpolations; and calculation of the thicknesses of the three categories of tissues penetrated according to this total length of attenuation and the two attenuations.

8 Claims, No Drawings

DUAL-ENERGY RADIOGRAPHY PROCESS DIFFERENTIATING BONE TISSUES, LEAN TISSUES AND FATTY TISSUES

This invention relates to a radiography process by means of dual-energy X or γ rays and comprises a differentiation among bone tissues, lean tissues and fatty tissues, above all for measurements of bone mineral content of an organism (osteodensitometry).

Using rays of two different energies to irradiate an organism and measuring their two attenuation by means of a surface detector system located behind the organism is well known. As a matter of fact, the attenuation ratios for the bone tissues and the soft tissues are not the same for both energies, with the result that the thicknesses of bone tissues and of soft tissues penetrated by the rays can be calculated, the numerical problem coming down to inverting a system of two equations with two unknowns for the measurements of each of the detectors affected by the rays which have penetrated the organism.

The results provided by this type of method, however, cannot be other than imprecise, since the tissues of living organisms also include fats, the absorption coefficients of which are different from those of the bone tissues and even the lean tissues.

Several attempts have been made to remedy this shortcoming of the basic process. It crosses one's mind that a third irradiation performed with rays of a third energy might make it possible to obtain a system of three equations the solution of which might yield the three penetrated thicknesses of the bone, lean and fatty tissues, but it turned out that in practice a sufficient precision could not be achieved because of the noise produced by the photons of the radiation and the need to limit the total dose of irradiation received by the organism. The article "Theoretical and experimental limits of triple photon energy absorptiometry in the measurement of bone mineral" by Kotzki et al. in the journal Phys. Med. Biol volume 36, 1991, pages 429 to 437, provides more detailed explanations.

In another process, referred to as "baseline method," the assumption is made that the proportion of fat is the same in the bone tissues and the soft tissues, but that does not always prove to be true, and the calculation then can be subject to rather substantial errors which can be as much as 20% of the thickness of the bone tissues. The article "Effect of nonmineral tissues on measurement of bone mineral content by dual-photon absorptionmetry" by Sorenson et al., Med. Phys. volume 17 (5), 1990, pages 905 to 912, is an illustration of this method.

Finally, the total thickness penetrated by the rays may constitute the additional piece of information needed to differentiate the three elements of the organisms. The article "Dual-photon absorptiometry for determination of bone mineral content in the calcaneus with correction of fat" by Jonson et al., Phys. Med. Biol., volume 35, number 7, 1990, pages 961 to 969, is an illustration thereof.

A source of error comes to light, however, when the studied portion of the organism contains gas pockets, because the total thickness penetrated no longer is the sum of the thicknesses of the bone, lean and fatty tissues and the method is thwarted. The purpose of the invention is to improve it and in particular to make it possible to obtain and to use the actual total of the thickness of the bone, lean and fatty tissues penetrated, rather than the thickness of the organism for the solution of the system. Thus, it relates to a radiography process with dual-energy rays comprising a differentiation among bone tissues, lean tissues and fatty tissues of an organism penetrated by the rays and estimations of thicknesses of the lean tissues, bone tissues and fatty tissues penetrated by the rays, characterized in that it comprises the following stages:

selection of certain rays, which have not penetrated bone tissues;

calculation of the thicknesses of lean tissues and fatty tissues penetrated by the selected rays according to the attenuations sustained in the two thicknesses of lean tissues and fatty tissues;

calculation of the sums of the total thicknesses penetrated by the rays in the organism, which are equal to the said sums for the selected rays and are estimated by means of interpolations between said sums for other rays;

and calculation of the thicknesses of bone tissues, lean tissues and fatty tissues penetrated by the rays according to the attenuations sustained at the two energies and the total thicknesses.

In more detailed manner, here is how one proceeds. The organism studied is subjected to an irradiation by rays with two energies by means of a beam which may be conical. The coefficients of attenuation of the bone, lean and fatty tissues are known for the two categories of rays. The table of total attenuation values measured, which corresponds to a two-dimensional double image of the organism, is set up. An approximate distribution of the bone tissues is derived therefrom, either by hypothesis or by an examination of the total attenuation values, which are appreciably greater when bones have been penetrated by the rays.

One then is concerned with the sites devoid of bone tissues. Knowledge of the two attenuations and of the coefficients for the lean and fatty tissues makes it possible easily to obtain the thicknesses of these two tissues respectively penetrated by the rays. Their sum is the total length of attenuation of the radiation by the organism at the site involved, the gas pockets being disregarded.

This total length of attenuation then is estimated everywhere else in the organism and in particular at the sites containing bone tissues. Linear or other interpolations may be used between the sites where the values thereof already have been obtained.

For each of the detectors, there then are available three pieces of information (the two attenuations and the total length of attenuation) as against three unknowns which are the penetrated lengths of the three tissue groups, or the penetrated masses thereof. The equation system can be in the form set forth below:

$$(\mu_{1m} \; \mu_{1g} \; \mu_{1os}) \quad (M_m) \quad (X_1)$$
$$(\mu_{2m} \; \mu_{2g} \; \mu_{2os}) \quad (M_g) = (X_2)$$
$$(1/\rho_m \; 1/\rho_g \; 1/\rho_{os}) \quad (M_{os}) \quad (L)$$

in which $M_m$, $M_g$ and $M_{os}$ designate the masses by unit of area (in g/cm$^2$) of lean, fatty and bone tissues penetrated by the radiation; $X_1$, $X_2$ and L designate the attenuations of the radiation (expressed by the logarithm of the intensity ratios of the original radiation $I_o$ and of the radiation I received by the detector involved: $X=\ln(I_o/I)$), and the total length of attenuation; $\mu_{1m}$, $\mu_{1g}$, $\mu_{1os}$, $\mu_{2m}$, $\mu_{2g}$ and $\mu_{2os}$ designate the coefficients of attenuation for the two radiations, of the lean, fatty and bone tissues in cm/g$^2$, and $\rho_m$, $\rho_g$ and $\rho_{os}$ are the densities of these tissues. The inversion of the system yields the values of $M_m$, $M_g$ and $M_{os}$, which can be correlated with the penetrated thicknesses of the lean, fatty and bone tissues $I_m$, $I_g$ and $I_{os}$ by means of the formulas $I_m=M_m/\rho_m$, $I_g=M_g/\rho_g$ and $I_{os}=M_{os}/\rho_{os}$.

In comparison with the classical baseline method, the application of the invention yielded very good results. In particular, a very good precision has been found in the main regions of the organisms, whereas the baseline method produced assessment errors at the sites of bone areas and especially of transition between bone areas and soft tissues.

The execution of the process explained in detail hereinabove is dependent on the assumption that the total penetrated length L is expressed by a linear function of the measurements $X_1$ and $X_2$. This assumption does not always prove to be true, in particular when the radiation is polychromatic: the length L then is expressed by a more complicated polynomial function such as $L=\alpha X_1+\beta X_2+\gamma X^2_1+\delta X_1 X_2+\epsilon X^2_2$.

Developing the foregoing process with stages in addition to these then is planned. The coefficients $\alpha$, $\beta$, $\gamma$, $\delta$ and $\epsilon$ are assessed by measurements of irradiation through wedges in sufficient number, which have different thicknesses of materials simulating the lean and fatty tissues, such as water and Plexiglas. The total length of attenuation L then can be calculated at all points of the object in accordance with the main process, directly at the sites devoid of bone and by means of interpolation elsewhere.

Next, as the lengths $I_m$, $I_g$ and $I_{os}$ then are expressed by nonlinear functions of $X_1$, $X_2$ and L, the coefficients of these functions are reassessed by measurements of irradiation through wedges, which here consist of different thicknesses of three materials, namely the preceding ones and a material simulating the bone tissues, such as hydroxyapatite. The lengths (or the masses) penetrated then can be obtained.

French patent application number 01 15849 filed Dec. 7, 2001, is incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A radiography process, comprising:
   irradiating an organism with dual energy rays;
   selecting rays which have not penetrated bone tissues;
   calculating a sum of a thickness of lean tissue and the thickness of fatty tissue penetrated by said selected rays according to an attenuation sustained at said thickness of said lean tissue and said thickness of said fatty tissue;
   calculating at least one total length penetrated by said selected rays in the organism which is equal to said sum of thickness of said lean tissue and said thickness of said fatty tissue for said selected rays; and
   estimating at least one other total length penetrated by said dual energy rays by interpolation between said sum of thickness of said lean tissue and said fatty tissue and a sum of thicknesses for rays different from said selected rays;
   calculating the thicknesses of bone tissues, lean tissues and fatty tissues penetrated by said dual energy rays according to the attenuations sustained at the two energies and the total lengths.

2. The method according to claim 1, wherein a conical beam is used for said irradiating.

3. The method according to claim 1, wherein the thicknesses or masses of said bone tissues, lean tissues and fatty tissues penetrated by said dual energy rays are calculated using the following equation system:

$$\begin{pmatrix} \mu_{1m} & \mu_{1g} & \mu_{1os} \\ \mu_{2m} & \mu_{2g} & \mu_{2os} \\ 1/\rho_m & 1/\rho_g & 1/\rho_{os} \end{pmatrix} \begin{pmatrix} M_m \\ M_g \\ M_{os} \end{pmatrix} = \begin{pmatrix} X_1 \\ X_2 \\ L \end{pmatrix}$$

wherein $M_m$, $M_g$ and $M_{os}$ designate the masses by unit of area, in g/cm$^2$, of lean, fatty and bone tissues penetrated by the rays;

$X_1$, $X_2$ and L designate the attenuations of the radiation, expressed by the logarithm of the intensity ratios of the original radiation Io and of the radiation I received by the detector involved: $X=\ln(I_o/I)$, and the total length of attenuation;

$\mu_{1m}$, $\mu_{1g}$, $\mu_{1os}$, $\mu_{2m}$, $\mu_{2g}$ and $\mu_{2os}$ designate the coefficients of attenuation for the two energies, of the lean, fatty and bone tissues in cm/g$^2$, and $\rho_m$, $\rho_g$ and $\rho_{os}$ are the densities of the lean, fatty and bone tissues.

4. The method according to claim 3, wherein said equation system yields the values of $M_m$, $M_g$ and $M_{os}$, which can be correlated with the penetrated thicknesses of the lean, fatty and bone tissues $I_m$, $I_g$, and $I_{os}$ by the following formulas $I_m=M_m/\rho_m$, $I_g=M_g/\rho_g$ and $I_{os}=M_{os}/\rho_{os}$.

5. The method according to claim 1, wherein the total penetrated length L is expressed by a linear function of the measurements $X_1$ and $X_2$.

6. The method according to claim 1, wherein said dual energy rays are polychromatic.

7. The method according to claim 1, wherein the total penetrated length L is expressed by the following polynomial function:

$$L=\alpha X_1+\beta X_2+\gamma X^2_1+\delta X_1 X_2+\epsilon X^2_2;$$

wherein $\alpha$, $\beta$, $\gamma$, $\delta$ and $\epsilon$ are coefficients which are assessed by measurements of irradiation through wedges.

8. An apparatus, comprising:
   a source for dual energy rays; and
   at least one detector;
   wherein said apparatus performs the method according to claim 1 for a differentiation among bone tissues, lean tissues and fatty tissues of an organism penetrated by dual energy rays and for estimations of thicknesses of the lean tissues, bone tissues and fatty tissues penetrated by the dual energy rays.

* * * * *